United States Patent
Watanabe

(10) Patent No.: US 12,150,624 B2
(45) Date of Patent: Nov. 26, 2024

(54) WATER/AIR SUPPLY NOZZLE FOR CLEANING AN OPTICAL LENS OF AN ENDOSCOPE

(71) Applicant: HOYA CORPORATION, Tokyo (JP)

(72) Inventor: Toshiki Watanabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 678 days.

(21) Appl. No.: 17/279,397

(22) PCT Filed: Mar. 13, 2020

(86) PCT No.: PCT/JP2020/011036
§ 371 (c)(1),
(2) Date: Mar. 24, 2021

(87) PCT Pub. No.: WO2020/203165
PCT Pub. Date: Oct. 8, 2020

(65) Prior Publication Data
US 2021/0386282 A1 Dec. 16, 2021

(30) Foreign Application Priority Data
Mar. 29, 2019 (JP) .................. 2019-068546

(51) Int. Cl.
*A61B 1/00* (2006.01)
*A61B 1/12* (2006.01)

(52) U.S. Cl.
CPC .......... *A61B 1/126* (2013.01); *A61B 1/00091* (2013.01); *A61B 1/00096* (2013.01); *A61B 1/00119* (2013.01)

(58) Field of Classification Search
CPC . A61B 1/126; A61B 1/00091; A61B 1/00096; A61B 1/00119; A61C 17/02
See application file for complete search history.

(56) References Cited

U.S. PATENT DOCUMENTS 5,871,440 A * 2/1999 Okada ............... A61B 1/00096
600/176
10,779,717 B2 9/2020 Kuwae et al.
(Continued)

FOREIGN PATENT DOCUMENTS

CN 101137319 A 3/2008
CN 104510434 A 4/2015
(Continued)

OTHER PUBLICATIONS

Official Communication issued in International Bureau of WIPO Patent Application No. PCT/JP2020/011036, dated Jun. 9, 2020.
(Continued)

*Primary Examiner* — Timothy J Neal
(74) *Attorney, Agent, or Firm* — GREENBLUM & BERNSTEIN, P.L.C.

(57) ABSTRACT

An endoscope, which is provided with an observation optical system provided at the tip of an insertion portion and a connecting pipe portion for sending a fluid onto the observation optical system side, includes a small diameter portion which has one end opening to which a fluid from the connecting pipe portion flows and has a diameter smaller than the connecting pipe portion, a lid portion which covers the other end opening of the small diameter portion, and a guide wall which is provided inside the lid portion to be separated from an edge of the other end opening in a radial direction of the other end opening and guides the fluid from the small diameter portion to an outlet.

5 Claims, 13 Drawing Sheets

(56) References Cited

U.S. PATENT DOCUMENTS

| | | | | |
|---|---|---|---|---|
| 2009/0247831 A1* | 10/2009 | Miyamoto | ......... | A61B 1/00091 600/157 |
| 2009/0253964 A1* | 10/2009 | Miyamoto | ......... | G02B 23/2476 600/157 |
| 2010/0010310 A1* | 1/2010 | Weisenburgh, II | .. | A61B 1/3132 600/156 |
| 2012/0197084 A1* | 8/2012 | Drach | ................ | A61B 1/00119 600/123 |
| 2012/0226104 A1 | 9/2012 | Ikeda et al. | | |
| 2014/0148647 A1* | 5/2014 | Okazaki | ................. | A61B 1/126 600/154 |

FOREIGN PATENT DOCUMENTS

| | | | |
|---|---|---|---|
| CN | 106063697 A | | 11/2016 |
| JP | 2003-210388 | | 7/2003 |
| JP | 2004-290457 | | 10/2004 |
| JP | 2007-244796 A | | 9/2007 |
| JP | 2007-252559 | | 10/2007 |
| JP | 2011-015774 | | 1/2011 |
| JP | 2011-212391 | | 10/2011 |
| JP | 2011212391 A | * | 10/2011 |
| JP | 2012-179221 | | 9/2012 |
| JP | 2012254137 A | * | 12/2012 |
| JP | 2013-034498 | | 2/2013 |
| JP | 2013-128660 | | 7/2013 |
| JP | 2013-220179 | | 10/2013 |
| JP | 2013220179 A | * | 10/2013 |

OTHER PUBLICATIONS

Official Action issued in Chinese Patent Application No. 202080005418.5, dated May 15, 2023.

Official Action issued in Japanese Patent Application No. 2022-106444, dated Mar. 28, 2023, together with an English-language translation.

\* cited by examiner

WATER/AIR SUPPLY NOZZLE FOR CLEANING AN OPTICAL LENS OF AN ENDOSCOPE

TECHNICAL FIELD

The present invention relates to an endoscope having an observation optical system at the tip of an insertion portion inserted into a body.

BACKGROUND ART

Conventionally, in an endoscope, an observation optical system for imaging a subject is provided at the tip of an insertion portion to be inserted into a body. Dirt such as mucus, blood and residue is likely to adhere to the surface of such an observation optical system. As described above, if the observation optical system is dirty or the like, it is difficult to take a clear image of the subject.

On the other hand, in the endoscope of Patent Literature 1 and the endoscope of Patent Literature 2, it is disclosed that a cleaning fluid is ejected onto a wall or a slope and collided with each other to widen the width of the fluid.

Further, in the distal end portion of the anterior-viewing endoscope of the Patent Literature 3 and an observation window cleaning nozzle of the endoscope of Patent Literature 4, it is disclosed that the outlet for ejecting the cleaning fluid is narrowed to make the fluid fast.

CITATION LIST

Patent Literature

Patent Literature 1: JP 2003-210388 A
Patent Literature 2: JP 2012-179221 A
Patent Literature 3: JP 2011-15774 A
Patent Literature 4: JP 2007-252559 A

SUMMARY OF INVENTION

Technical Problem

On the other hand, the needs for higher image quality and wider field of view of endoscopes are increasing, and the observation optical system is becoming larger. For cleaning a large observation optical system, it is necessary that the cleaning fluid is emitted at high speed and over a wide range.

However, in the endoscope of Patent Literature 1 and the endoscope of Patent Literature 2 described above, the cleaning fluid is ejected onto a wall or a slope and collided with each other to widen the width with respect to the large observation optical system. However, a larger slope is required, which is not possible physically, and the slope is too steep, so the fluid speed due to the collision is reduced, or the fluid is separated from the surface of the distal end portion of the endoscope due to a steep gradient. Further, in the distal end portion of the anterior-viewing endoscope of Patent Literature 3 and the observation window cleaning nozzle of the endoscope of Patent Literature 4, since the outlet is narrowed to increase the fluid speed, the speed of the fluid is reduced when the outlet is widened in correspondence with the large observation optical system. Therefore, the problem of compatibility between high speed and a wide range cannot be solved.

The invention has been made in view of such circumstances, and an object of the invention is to provide an endoscope which can eject a cleaning fluid at high speed and over a wide range and can sufficiently clean the entire surface of the observation optical system.

Solution to Problem

An endoscope according to the invention is provided with an observation optical system provided at a tip of an insertion portion and a fluid pipe portion for sending a fluid onto the observation optical system side. There is included a small diameter portion which has one end opening to which a fluid from the fluid pipe portion flows and has a diameter smaller than the fluid pipe portion, a lid portion that covers another end opening of the small diameter portion, and a guide wall that is provided inside the lid portion to be separated from an edge of the other end opening in a radial direction of the other end opening, and guides the fluid from the small diameter portion to an outlet.

In the invention, since the small diameter portion has a smaller diameter than the fluid pipe portion, the flow speed of the fluid flowing into the small diameter portion becomes faster, and after flowing out from the other end opening of the small diameter portion, the fluid is guided to the outlet by the guide wall. At this time, a fluid vortex is formed between the other end opening of the small diameter portion and the guide wall, so that the fluid flows at high speed and easily diffuses.

Advantageous Effects of Invention

According to the invention, the cleaning fluid can be ejected at high speed and over a wide range, and the entire surface of the observation optical system can be sufficiently cleaned.

DESCRIPTION OF EMBODIMENTS

Hereinafter, an endoscope according to embodiments of the invention will be described in detail with reference to the drawings.

First Embodiment

Figure 1:
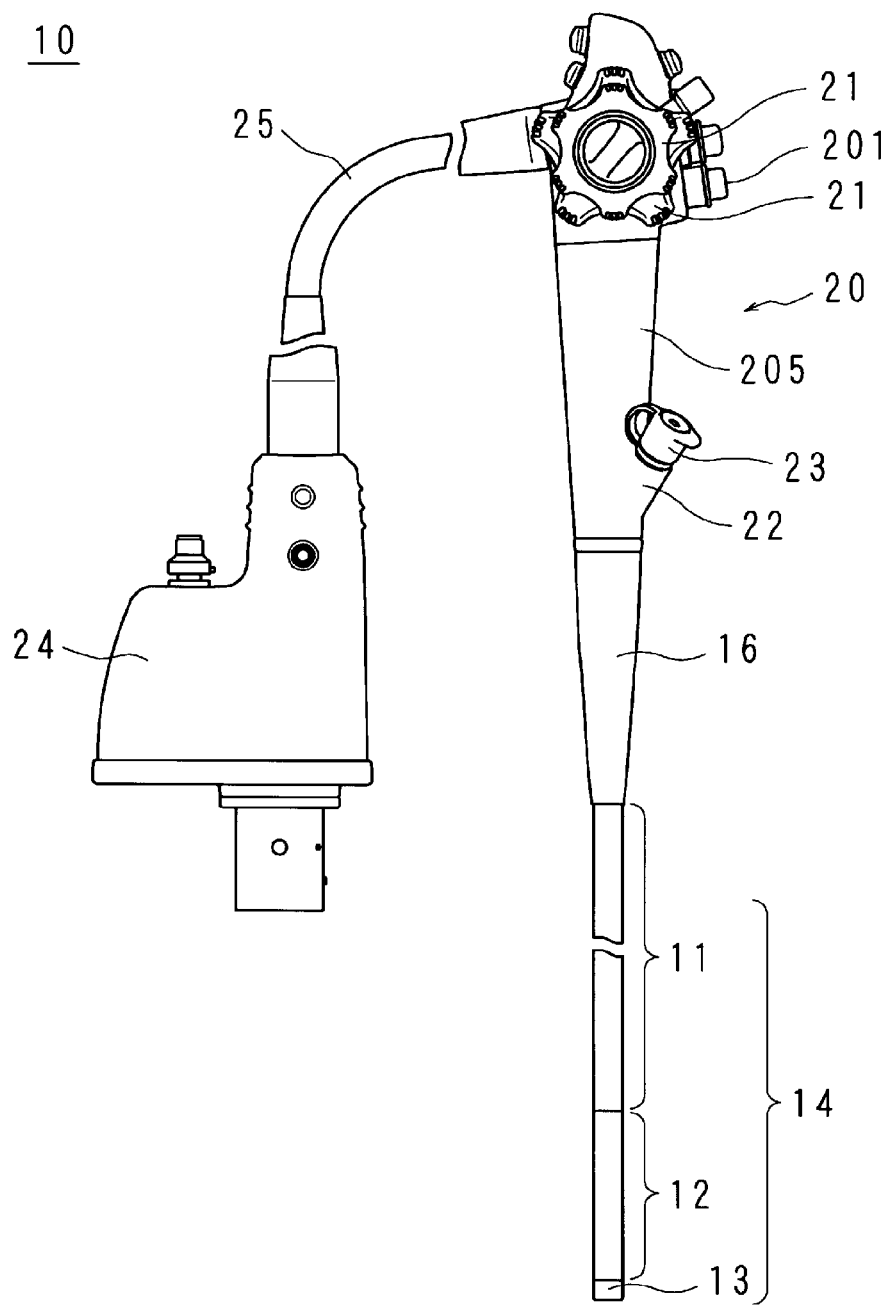
FIG. 1 is an external view of an endoscope according to a first embodiment of the invention.

FIG. 1 is an external view of an endoscope 10 according to the first embodiment of the invention. The endoscope 10 according to this embodiment includes an insertion portion 14, an operation unit 20, a universal cord 25, and a connector unit 24. The operation unit 20 includes a button 201 and a bending knob 21 for receiving a user operation, and a channel inlet 22 provided in a case 205 having a substantially cylindrical shape. A forceps plug 23 having an insertion port for inserting a treatment tool or the like is fixed to the channel inlet 22.

The insertion portion 14 is inserted into the body of a subject. The insertion portion 14 is long and has a distal end portion 13, a bending portion 12, and a soft portion 11 in this order from one end of the tip. The other end of the insertion portion 14 is connected to the operation unit 20 via a folding portion 16. The bending portion 12 is bent according to an operation of a bending knob 21.

In the following description, the other end side close to the operation unit 20 in the longitudinal direction of the insertion portion 14 is referred to as an operation unit side, and the one end side close to the distal end portion 13 is also referred to as a distal end portion side.

The universal cord 25 is long, and has one end connected to the operation unit 20 and the other end connected to the connector unit 24. The universal cord 25 is soft. The connector unit 24 is connected to an endoscope processor (not illustrated), a light source device, a display device, an air supply/water supply device, and the like. By appropriately operating the operation unit 20, the cleaning fluid (air or water) sent through the connector unit 24 is sent to the distal end portion 13 via the folding portion 16.

Figure 2:
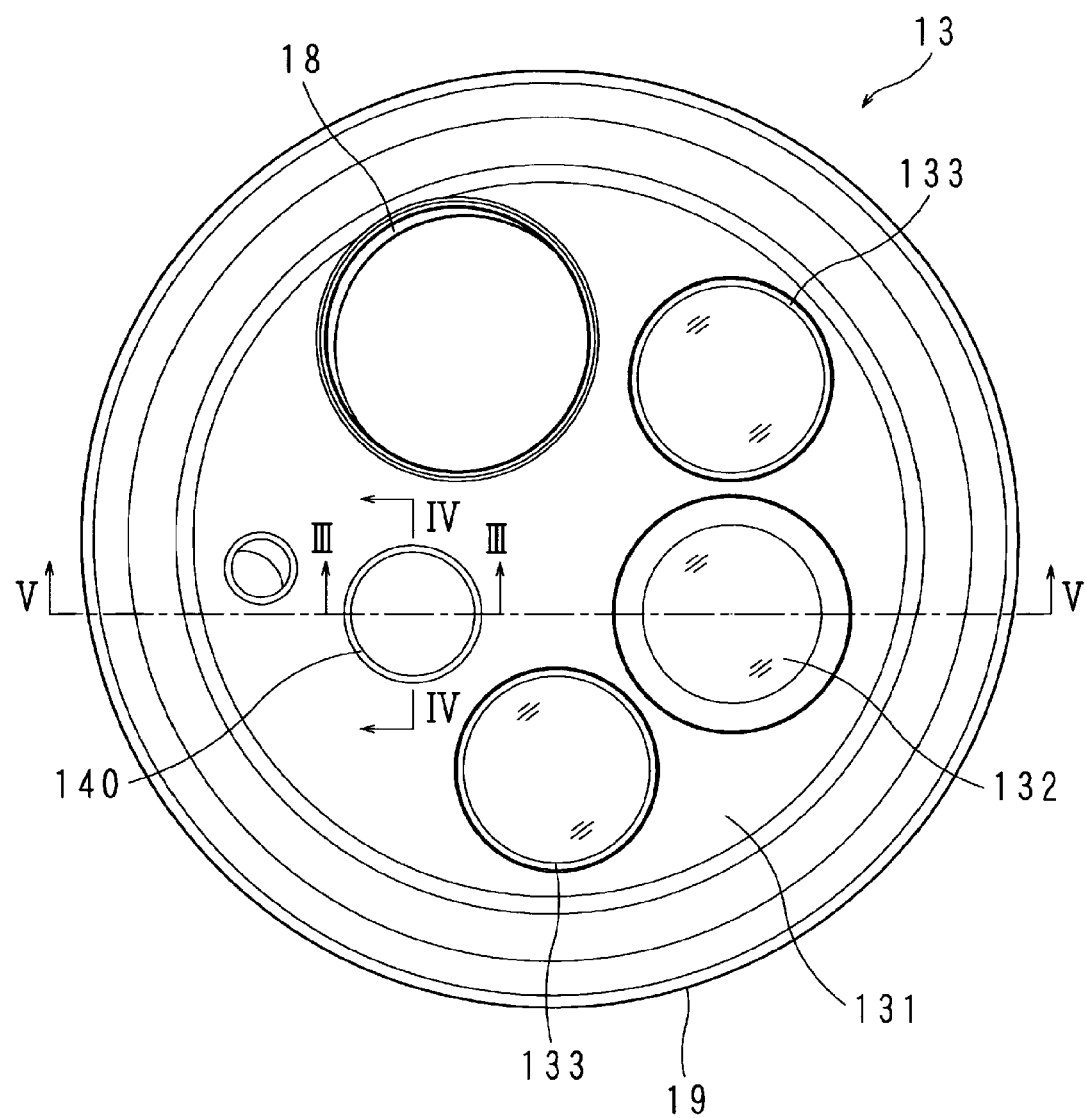
FIG. 2 is an external view of a distal end portion of the endoscope according to the first embodiment of the invention.

FIG. 2 is an external view of the distal end portion 13 of the endoscope 10 according to the first embodiment of the invention. The distal end portion 13 is circular in cross section, and a distal end surface 131 of the distal end portion 13 is a flat surface. The distal end surface 131 of the distal end portion 13 is provided with an observation optical system 132, an air supply/water supply nozzle 140, a channel outlet 18, an illumination optical system 133, and the like.

Further, the distal end portion 13 has a cylindrical storage cylinder 19 which houses an image sensor (not illustrated) or the like that captures the image light of the subject via the observation optical system 132 and performs imaging. The distal end surface 131 of the distal end portion 13 extends from the edge of a storage cylinder 19. Channels for injecting air and water to the observation optical system 132 via the air supply/water supply nozzle 140 is formed in the storage cylinder 19, the bending portion 12, and the soft portion 11.

Two illumination optical systems 133 are provided on the distal end surface 131 so as to be separated from each other, and the observation optical system 132 is provided between the two illumination optical systems 133. The observation optical system 132 on the distal end surface 131 is a flat surface. Further, on the distal end surface 131, an air supply/water supply nozzle 140 and a channel outlet 18 are provided at a distance from the observation optical system 132.

The air supply/water supply nozzle 140 injects air or water toward the observation optical system 132, and the illumination optical system 133 emits irradiation light to illuminate the object.

Figure 3:
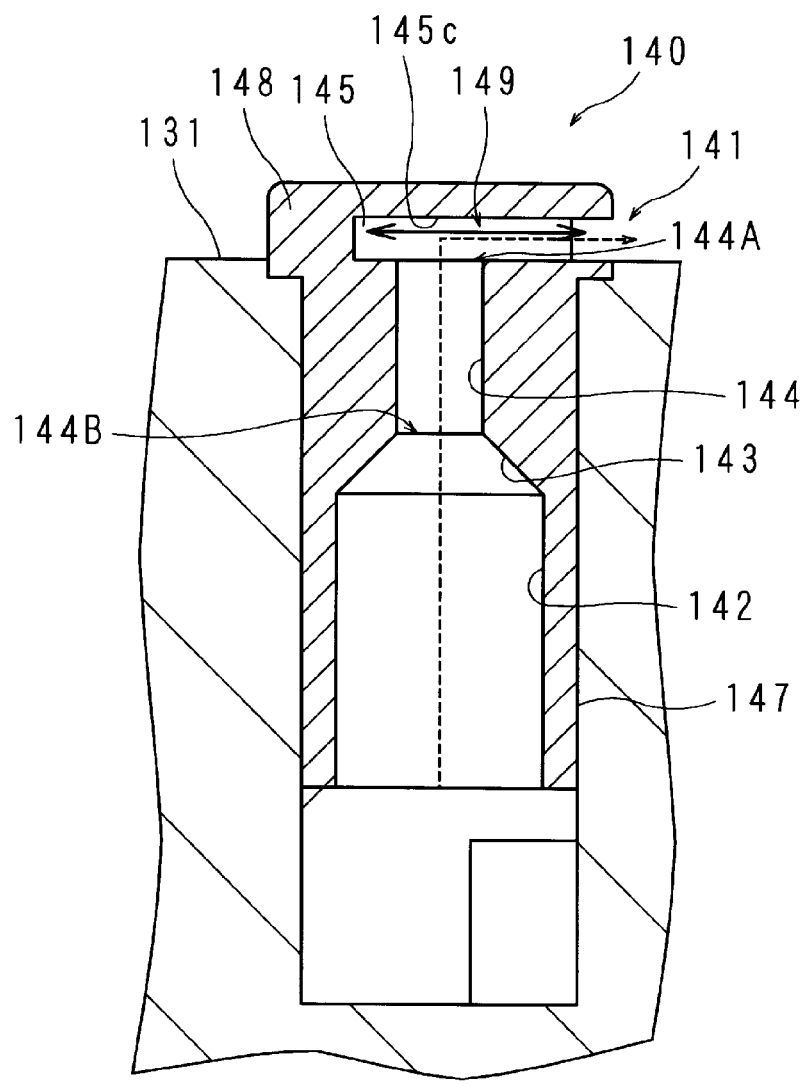
FIG. 3 is a cross-sectional view of the endoscope taken along line III-III of FIG. 2.
Figure 4:
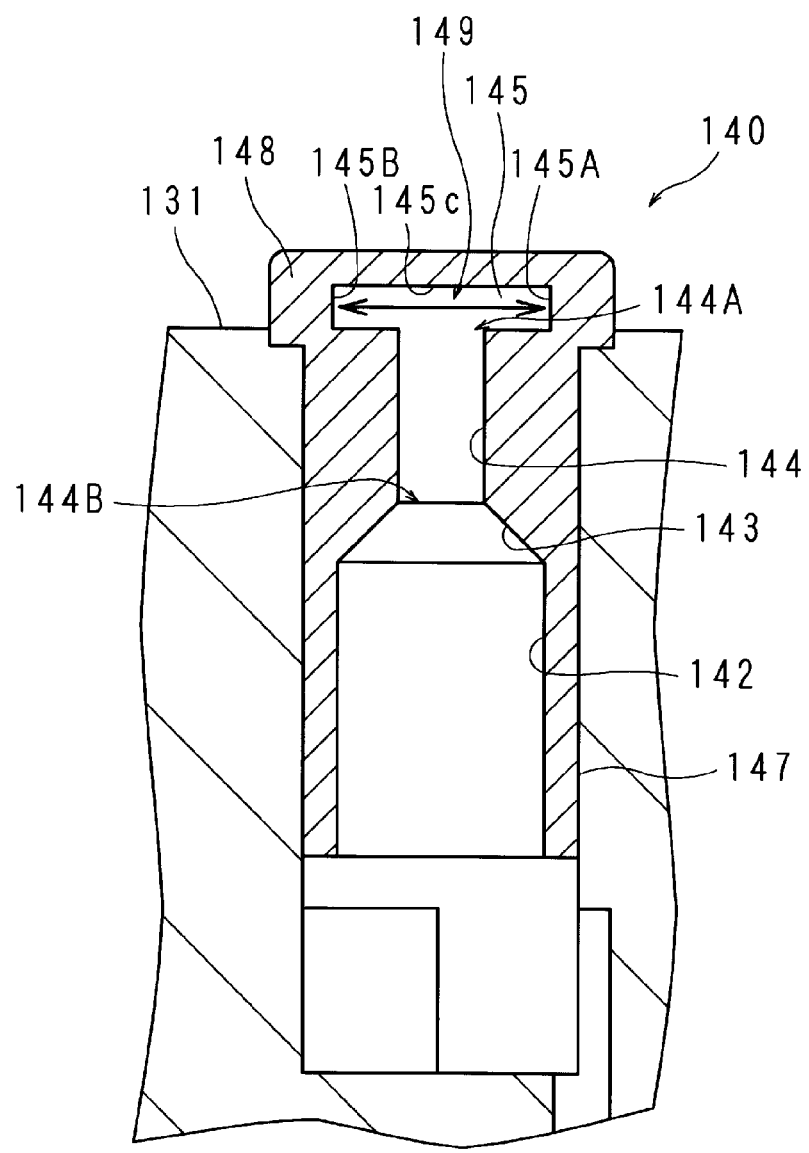
FIG. 4 is a cross-sectional view of the endoscope taken along line IV-IV in FIG. 2.
Figure 5:
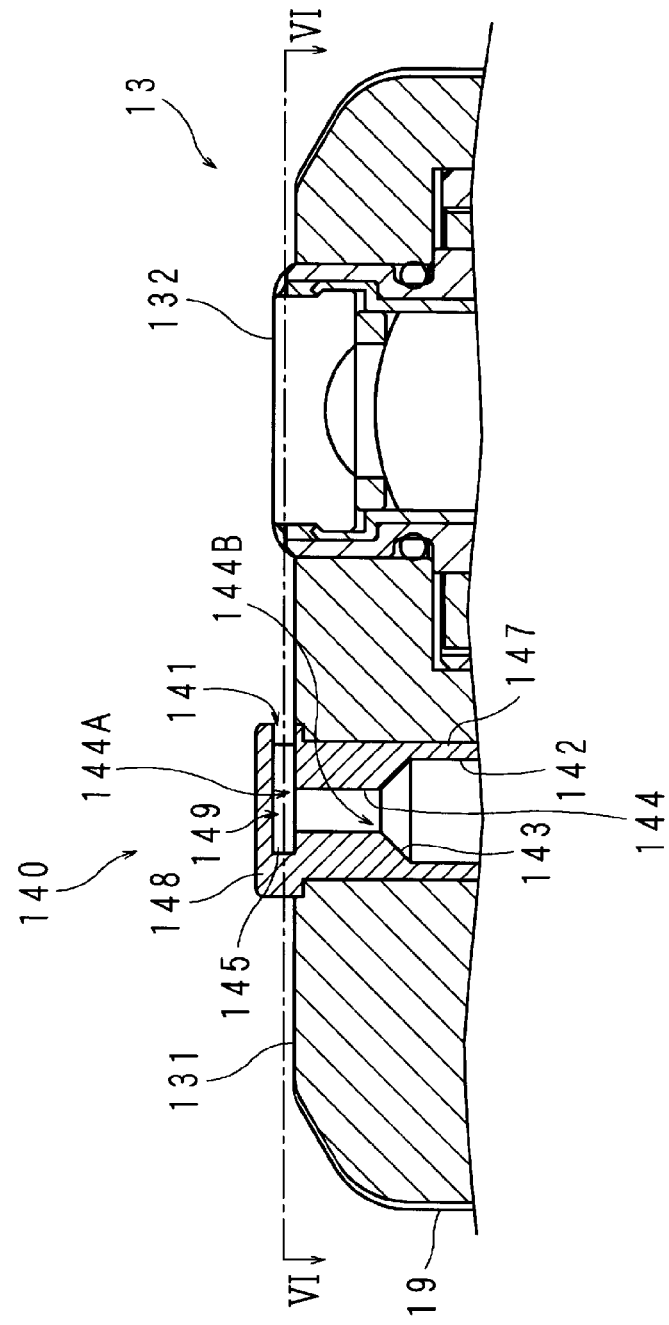
FIG. 5 is a cross-sectional view of the endoscope taken along line V-V of FIG. 2.
Figure 6:
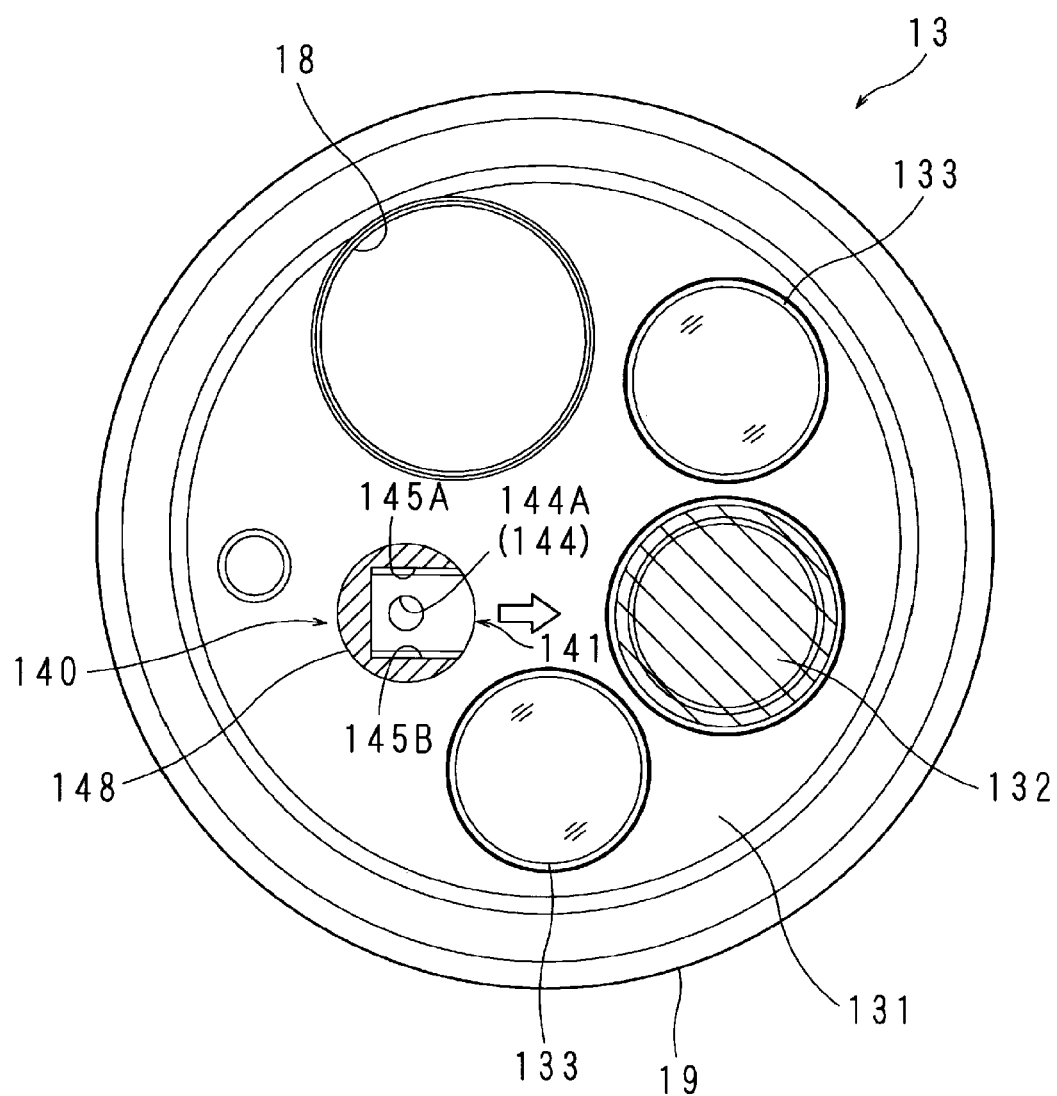
FIG. 6 is a cross-sectional view taken along line VI-VI of FIG. 5.

FIG. 3 is a cross-sectional view taken along line III-III of FIG. 2, FIG. 4 is a cross-sectional view taken along line IV-IV of FIG. 2, FIG. 5 is a cross-sectional view taken along line V-V of FIG. 2, and FIG. 6 is a cross-sectional view taken along line VI-VI of FIG. 5.

The air supply/water supply nozzle 140 injects air or water toward the observation optical system 132 along the distal end surface 131 (see arrows of FIGS. 3 and 6). The air supply/water supply nozzle 140 has an outlet 141 from which air or water is emitted. Air and water are emitted toward the observation optical system 132 via the outlet 141. The outlet 141 has a substantially oval shape.

Most of the air supply/water supply nozzle 140 is inserted and fixed in the recess provided in the distal end surface 131.

The air supply/water supply nozzle 140 has a cylinder portion 147 and a lid portion 148 that seals one open end of the cylinder portion 147. The lid portion 148 and the cylinder portion 147 are integrally formed. The outlet 141 is provided on the lid portion 148 side in the air supply/water supply nozzle 140.

A connecting pipe portion 142 (fluid pipe portion) and a small diameter portion 144 are provided inside the cylinder portion 147, and a diameter-reduced portion 143 is formed between the connecting pipe portion 142 and the small diameter portion 144.

The connecting pipe portion 142 extends along the longitudinal direction of the cylinder portion 147, and air or water sent from the connector unit 24 and the folding portion 16 side via an air supply tube and a water supply tube (not illustrated) is sent to the outlet 141. The connecting pipe portion 142 connects the air supply tube and the water supply tube with the small diameter portion 144. The air or water that has flowed into one end of the connecting pipe portion 142 is sent to the outlet 141 via the small diameter portion 144.

The small diameter portion 144 is provided at the other end (the end on the lid portion 148 side) on the downstream side of the connecting pipe portion 142 via the diameter-reduced portion 143. The small diameter portion 144 has a smaller diameter than the connecting pipe portion 142. The air or water that has flowed into the small diameter portion 144 is emitted through the outlet 141.

As described above, the diameter-reduced portion 143 is formed on the downstream side of the connecting pipe portion 142 and on the upstream side of the small diameter portion 144. The diameter-reduced portion 143 connects the other end of the connecting pipe portion 142 and one end of the small diameter portion 144 (one end opening 144B). The diameter-reduced portion 143 has a tapered shape or a funnel shape. That is, in the diameter-reduced portion 143, the diameter is gradually reduced from the connecting pipe portion 142 toward the small diameter portion 144. Therefore, the pressure of the air or water flowing into the small diameter portion 144 through the diameter-reduced portion 143 is reduced and the flow speed is increased.

The connecting pipe portion 142, the diameter-reduced portion 143, and the small diameter portion 144 are provided around the same axis.

The lid portion 148 has a disk shape having a predetermined thickness, and is provided so as to intersect the parallel arrangement direction of the connecting pipe portion 142, the diameter-reduced portion 143, and the small diameter portion 144. A guide path 149 is formed inside the lid portion 148. The guide path 149 is a cavity cut out in a flat rectangular shape, and guides the air or water flowing out from the other end opening 144A to the outlet 141. That is, the guide path 149 includes a side wall 145 (guide wall) parallel to the thickness direction of the lid portion 148 and a ceiling wall 145C orthogonal to the side wall 145. The guide path 149 communicates with the outside through the outlet 141.

The air or water that has flowed into one end of the connecting pipe portion 142 is injected through the diameter-reduced portion 143, the small diameter portion 144, the guide path 149, and the outlet 141. In FIG. 3, the air or water flow path is illustrated by a broken line.

The lid portion 148 is provided so as to cover the other end opening 144A of the small diameter portion 144. Specifically, the end of the small diameter portion 144 on the downstream side communicates with the guide path 149 at the central portion of the lid portion 148. That is, the other end opening 144A of the small diameter portion 144 is connected to the guide path 149.

The side wall 145 surrounds the other end opening 144A of the small diameter portion 144 in a U-shape, and guides air or water from the other end opening 144A to the outlet 141 (see FIG. 6). The other end opening 144A of the small diameter portion 144 is, for example, circular, and the side wall 145 is formed at a position separated from the edge of the other end opening 144A in the radial direction of the other end opening 144A.

That is, in the facing direction (the direction of the solid line arrow in FIG. 4) of the side wall 145A and the side wall 145B (two facing portions) facing each other in the side wall 145, the dimension between the side wall 145A and the side wall 145B is longer than the diameter of the other end opening 144A. Further, the side wall 145 is provided away from the edge of the other end opening 144A also in the crossing direction intersecting the facing direction (the direction of the solid line arrow in FIG. 3), that is, in the direction connecting the other end opening 144A and the outlet 141.

Further, the other end opening 144A is provided in the intermediate portion between the side wall 145A and the side wall 145B in the facing direction. Further, the other end opening 144A is provided closer to the side wall 145 than the outlet 141 in the crossing direction.

The dimension between the side wall 145A and the side wall 145B in the facing direction is equal to or less than the dimension of the outlet 141 in the facing direction. That is, in the facing direction, the dimension between the side wall 145A and the side wall 145B is the same as that of the outlet 141, or is provided so as to increase as it approaches the outlet 141.

Since it has such a configuration, in the endoscope 10 according to this embodiment, high-speed air or water can be ejected toward the observation optical system 132 in a wide range.

As described above, in the cavity in the guide path 149, the cross-sectional area of the other end opening 144A in the radial direction is larger than the area of the other end opening 144A. That is, since the width of the cavity in the guide path 149 is wider than that of the other end opening 144A, when air or water having a higher speed after the passage of the small diameter portion 144 flows out from the other end opening 144A, it spreads in the guide path 149 and maintains the speed faster than the connecting pipe portion 142. At this time, a vortex flow is formed around the other end opening 144A, and air or water flows at high speed and easily diffuses around the other end opening 144A.

That is, as described above, in the diameter-reduced portion 143, the diameter is gradually reduced from the connecting pipe portion 142 toward the small diameter portion 144, so that the flow speed of the air or water flowing into the small diameter portion 144 through the diameter-reduced portion 143 becomes faster. The air or water having a higher flow speed flows out from the other end opening 144A and is guided by the ceiling wall 145C and the side wall 145 to form a vortex flow around the other end opening 144A. Therefore, the air or water diffuses uniformly in the guide path 149. Therefore, when the air or water is emitted from the outlet 141, it easily spreads in the width direction (direction of arrow in FIG. 9), and the injection force at the time of emission can be secured.

Further, the other end opening 144A is provided in the intermediate portion between the side wall 145A and the side wall 145B in the facing direction. That is, since the side wall 145A and the side wall 145B are separated from the edge of the other end opening 144A by substantially the same distance, a vortex flow of the same size is formed, and the speed of air or water can be made more uniform.

Further, as described above, the other end opening 144A is provided closer to the side wall 145 than the outlet 141 in the crossing direction. That is, in the crossing direction, the other end opening 144A to the outlet 141 is a wide region including a region where a vortex flow is formed. Therefore, after the air or water forms a vortex flow around the other end opening 144A, it does not immediately emitted through the outlet 141, but flows in the guide path 149 for a while. Therefore, at this time, the air or water is emitted from the outlet 141 toward the observation optical system 132 after the flow direction and the like are rectified. Therefore, it is possible to prevent the air or water from traveling in a different direction after passing through the outlet 141. For example, it is possible to prevent the air or water from traveling away from the distal end surface 131 (a plane of the observation optical system 132) in a direction orthogonal to the distal end surface 131 (a plane of the observation optical system 132).

Moreover, the dimension between the side wall 145A and the side wall 145B in the facing direction is equal to or less than the dimension of the outlet 141 in the facing direction. Therefore, it is possible to prevent the air or water toward the outlet 141 from colliding with the side wall 145A and the side wall 145B and slowing down, and the air or water is emitted from the outlet 141 at a high speed.

Figure 7:
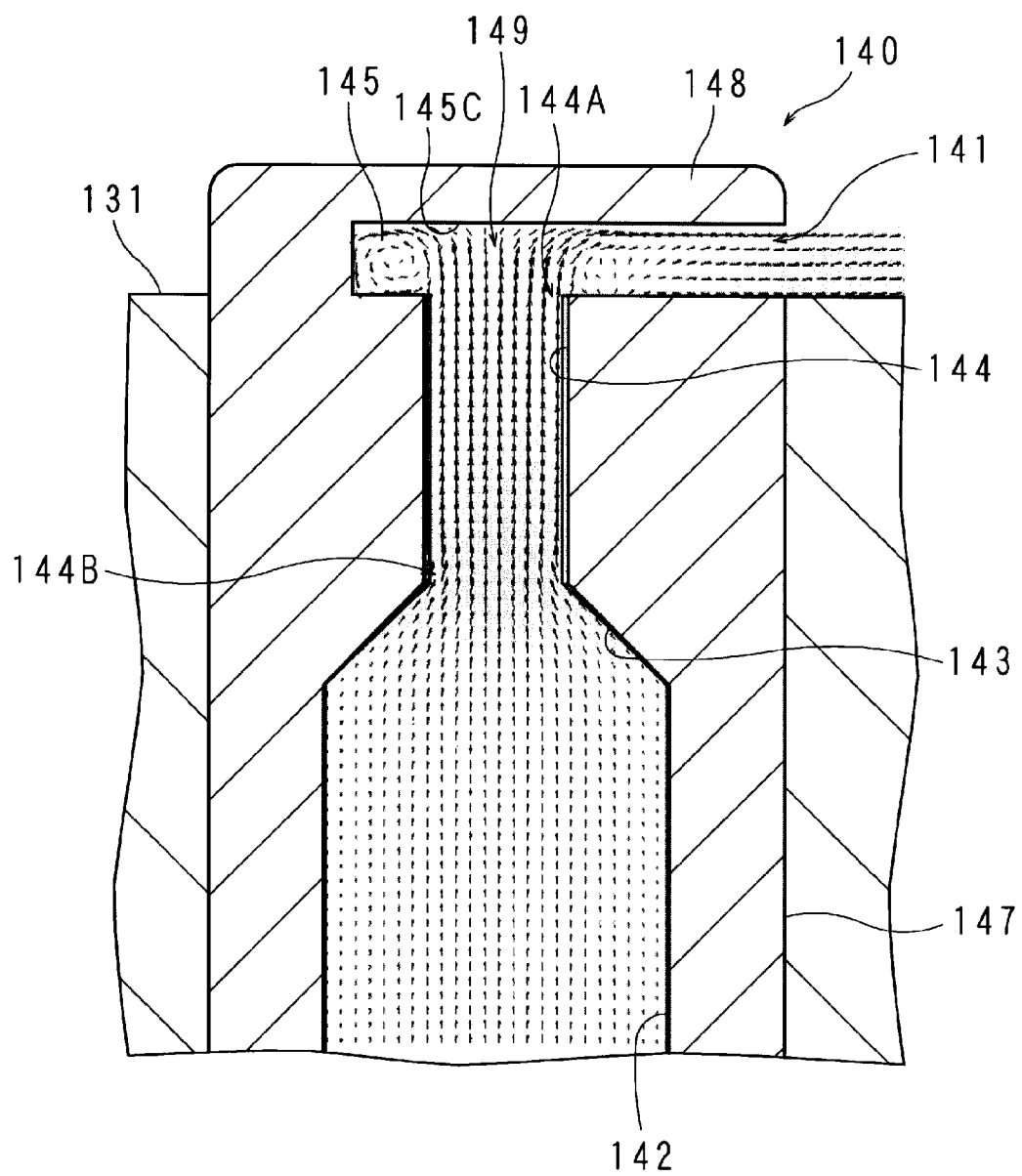
FIG. 7 is a diagram illustrating a result of simulating the flow of cleaning water in an air supply/water supply nozzle of the endoscope according to the first embodiment of the invention.
Figure 8:
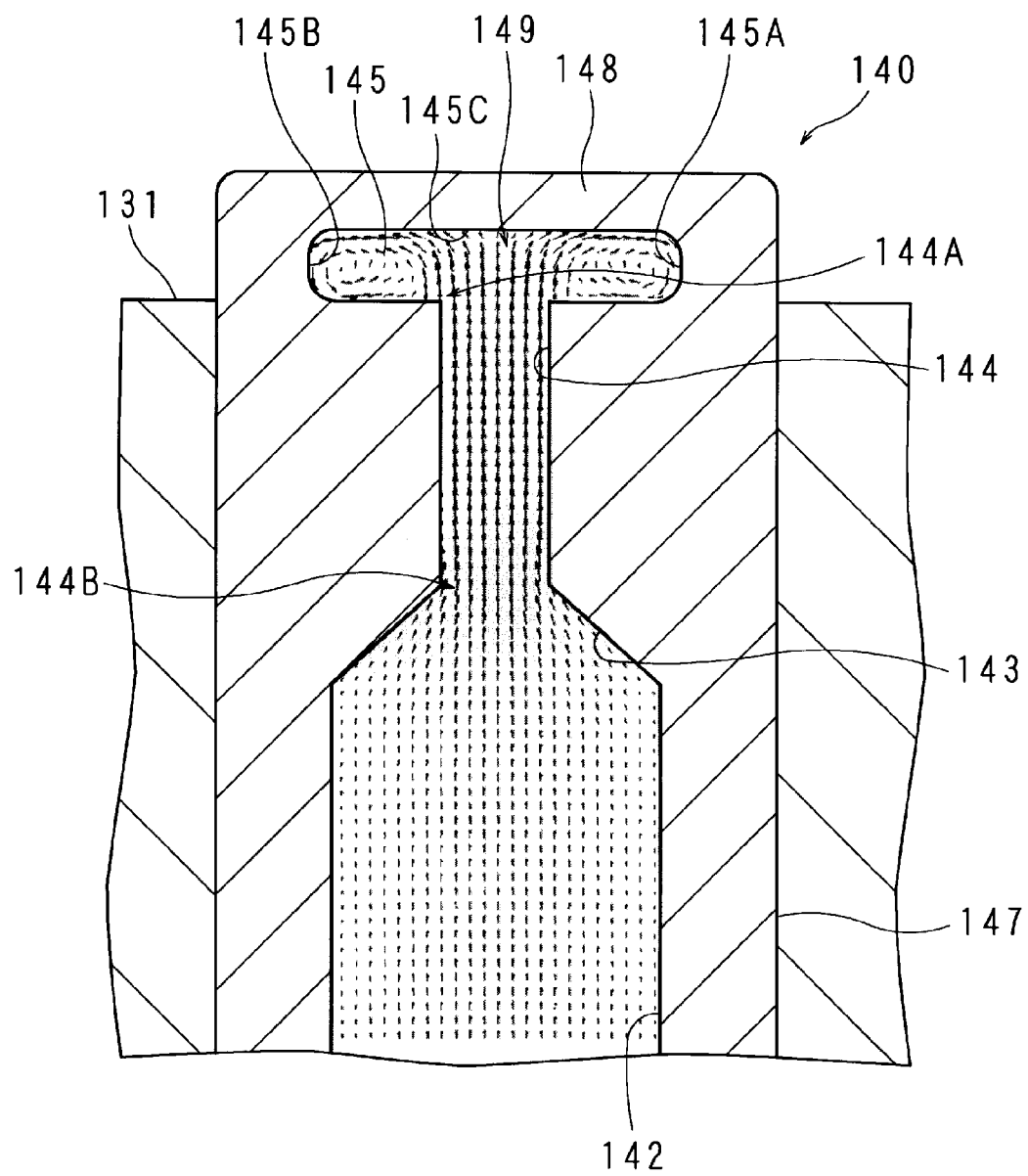
FIG. 8 is a diagram illustrating a result of simulating the flow of cleaning water in the air supply/water supply nozzle of the endoscope according to the first embodiment of the invention.
Figure 9:
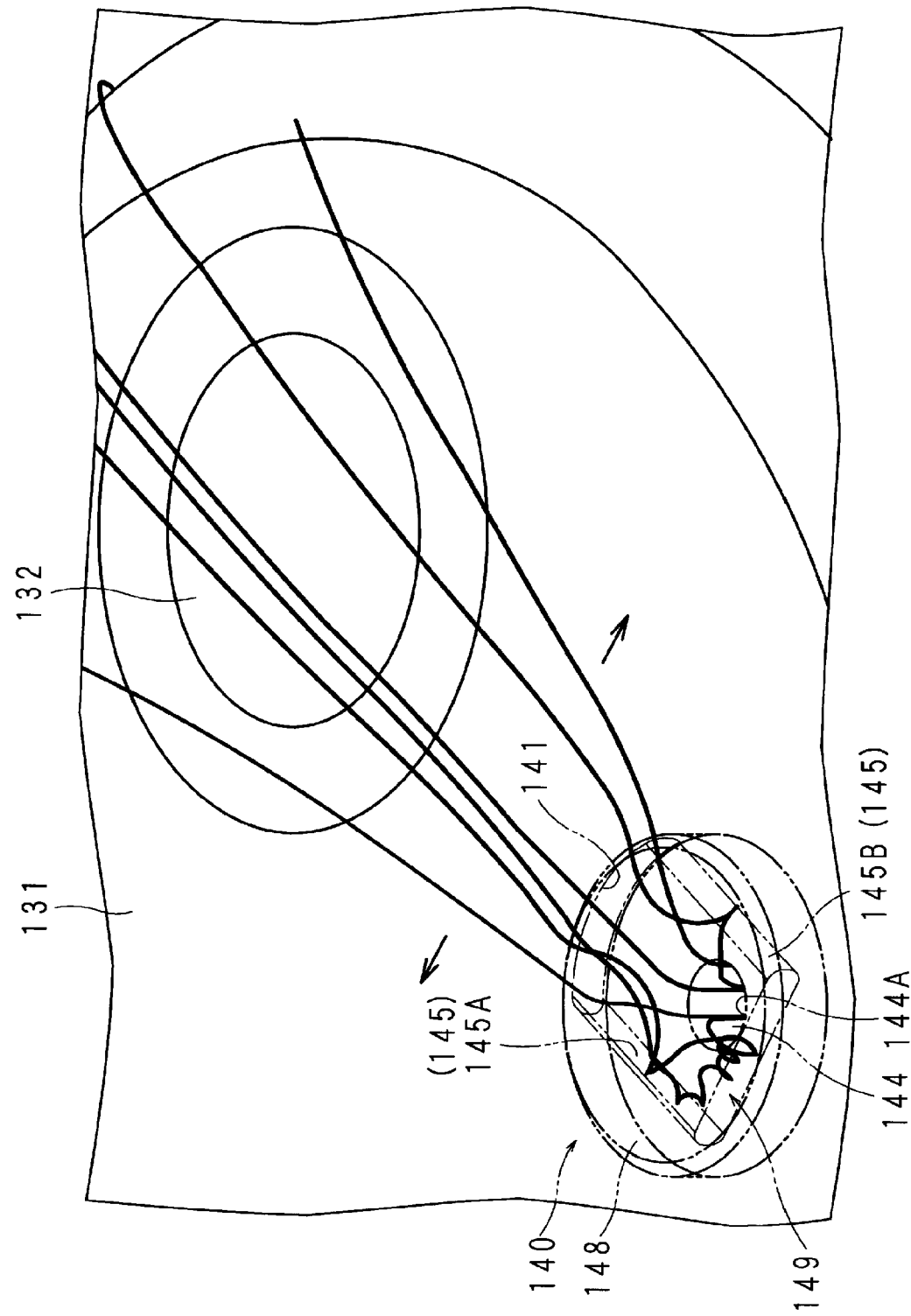
FIG. 9 is a diagram illustrating a result of simulating the flow of cleaning water in the air supply/water supply nozzle of the endoscope according to the first embodiment of the invention.

FIGS. 7 to 9 are diagrams illustrating the results of simulating the flow of cleaning water in the air supply/water supply nozzle 140 of the endoscope 10 according to the first embodiment of the invention. The flow of cleaning air is the same as the simulation results of FIGS. 7 to 9, and the detailed description is omitted.

FIG. 7 illustrates the results of the simulation with respect to the cross-sectional view of FIG. 3, and FIG. 8 illustrates the results of the simulation with respect to the cross-sectional view of FIG. 4. In FIGS. 7 and 8, the flow and magnitude of the cleaning water are illustrated as vectors. That is, in FIGS. 7 and 8, the flow direction of the cleaning water is indicated by the direction of arrow, and the speed of the cleaning water is indicated by the length of arrow.

As can be seen from FIGS. 7 and 8, the cleaning water increases in speed as it passes from the connecting pipe portion 142 to the diameter-reduced portion 143, and flows into the small diameter portion 144. The cleaning water flowing out from the small diameter portion 144 (the other end opening 144A) forms a vortex flow around the other end opening 144A. After that, the cleaning water flows in the guide path 149 toward the outlet 141 without slowing down, and at this time, rectification is performed. The rectified cleaning water is emitted from the outlet 141, but no reduction in speed is observed before and after the emission.

FIG. 9 is a diagram illustrating the flow of cleaning water from the other end opening 144A to the observation optical system 132. For convenience of explanation, the other end opening 144A and the lid portion 148 are illustrated by a chain double-dashed line, assuming that the lid portion 148 is transparent. Further, in FIG. 9, the flow of the cleaning water is illustrated by a thick solid line, but for convenience of drawing, it is illustrated by only six lines.

As can be seen from FIG. 9, the cleaning water flowing out from the other end opening 144A forms a vortex flow around the other end opening 144A, is rectified, and then is emitted from the outlet 141. After emission, the cleaning water begins to spread in the width direction (the direction of arrow in FIG. 9), and when it reaches the observation optical system 132, it spreads over a wider area than the area of the observation optical system 132.

As described above, in the endoscope 10 according to the first embodiment of the invention, the cleaning air or water has a high speed and does not change in speed before and after being emitted from the outlet 141 of the air supply/water supply nozzle 140, and ejected to the observation optical system 132. Moreover, since the air or water ejected from the air supply/water supply nozzle 140 spreads over a wider area than the area of the observation optical system 132, the entire surface of the observation optical system 132 can be cleaned cleanly.

Second Embodiment

Figure 10:
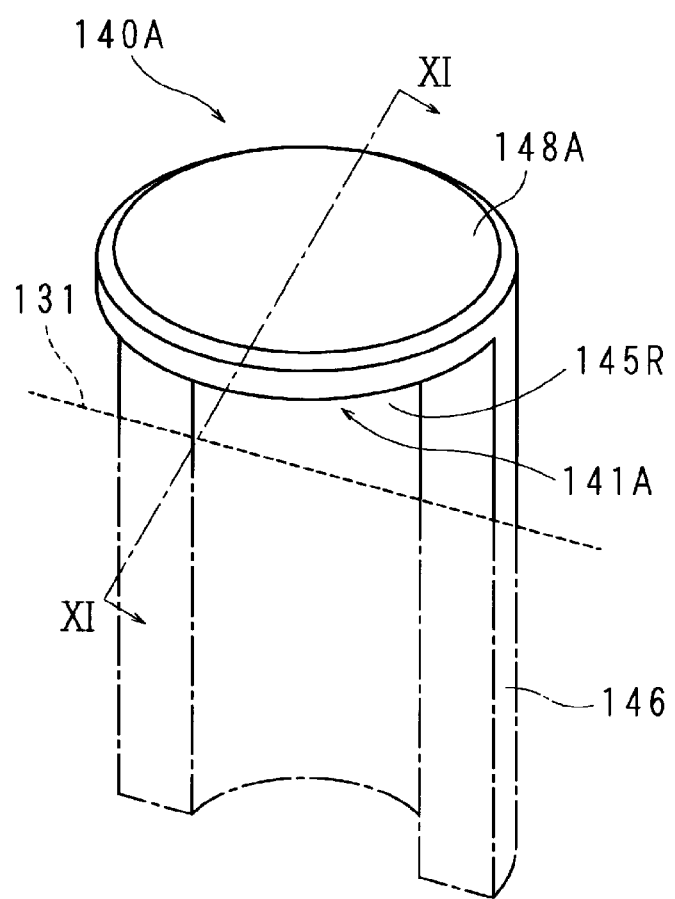
FIG. 10 is a perspective view illustrating an air supply/water supply nozzle of the endoscope according to a second embodiment of the invention.

FIG. 10 is a perspective view illustrating an air supply/water supply nozzle 140A of the endoscope 10 according to the second embodiment of the invention. In FIG. 10, the portion to be inserted into the recess provided on the distal end surface 131 in the air supply/water supply nozzle 140A is indicated by a chain line, and the distal end surface 131 is indicated by a broken line.

The air supply/water supply nozzle 140A of the endoscope 10 according to the second embodiment of the invention has a semi-cylindrical portion 146 inserted into a recess provided on the distal end surface 131, and one open end of the semi-cylindrical portion 146 is sealed by a lid portion 148A. The lid portion 148A and the semi-cylindrical portion 146 are integrally formed.

The lid portion 148A has a disk shape and is orthogonal to the longitudinal direction of the semi-cylindrical portion 146. The lid portion 148A has substantially the same radius as the semi-cylindrical portion 146, and the one open end of the semi-cylindrical portion 146 is provided along the peripheral edge of the lid portion 148A. The area of one surface of the lid portion 148A is larger than the cross-sectional area of the semi-cylindrical portion 146 in the radial direction, and a part of the lid portion 148A protrudes from the semi-cylindrical portion 146 in the radial direction of the semi-cylindrical portion 146. Hereinafter, the part of the lid portion 148A is referred to as a protruding portion.

Figure 11:
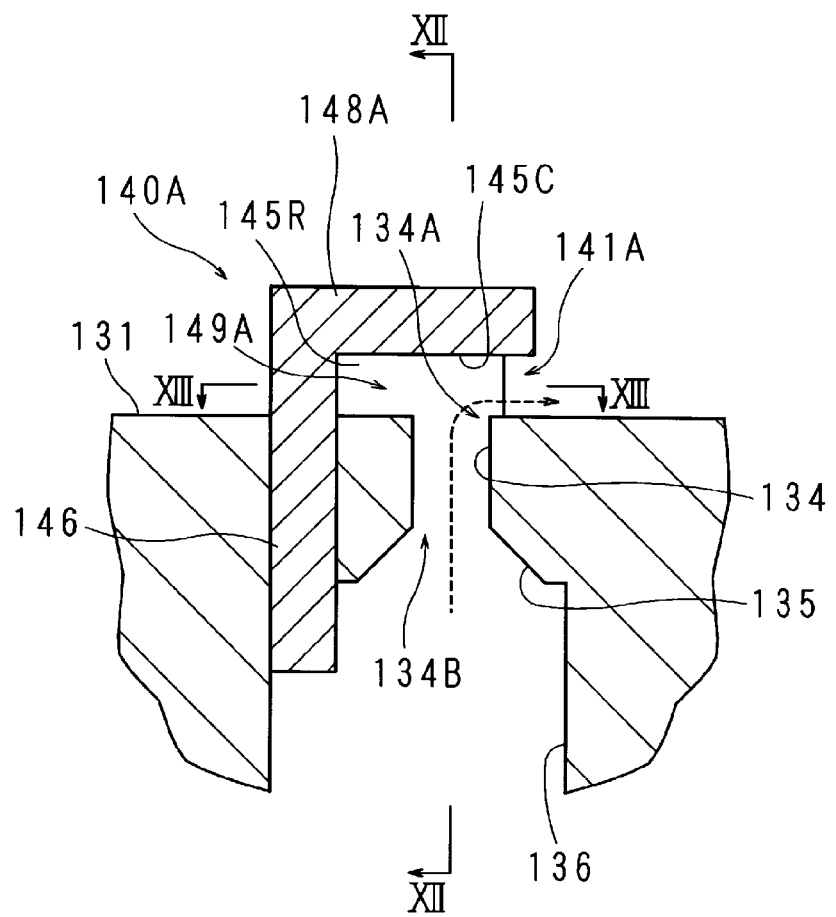
FIG. 11 is a cross-sectional view of the distal end portion taken along line XI-XI of FIG. 10 when the air supply/water supply nozzle is attached to the distal end portion.
Figure 12:
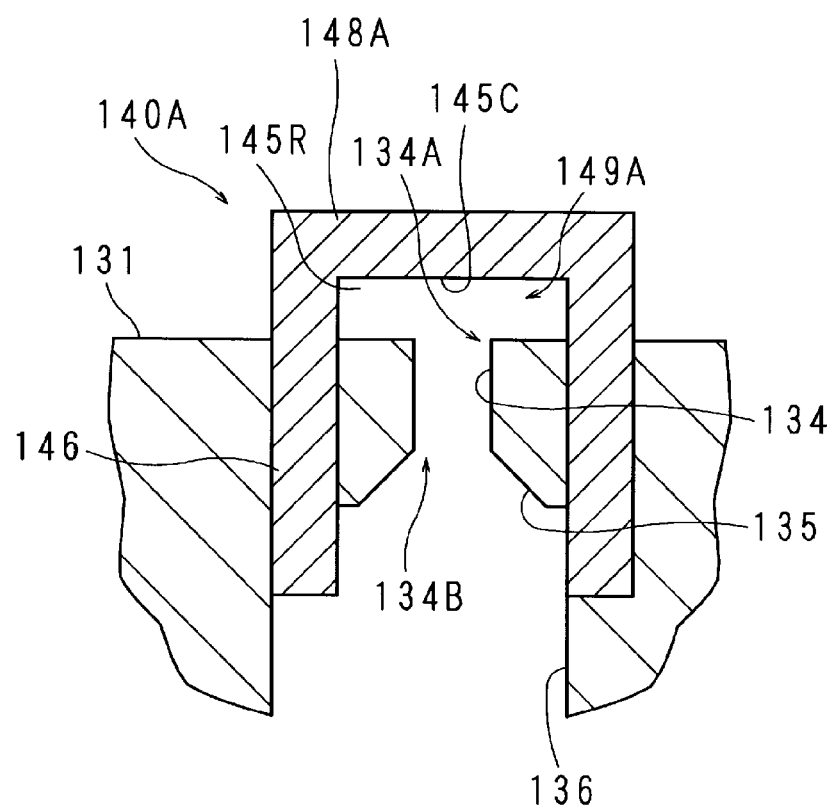
FIG. 12 is a cross-sectional view taken along line XII-XII of FIG. 11.
Figure 13:
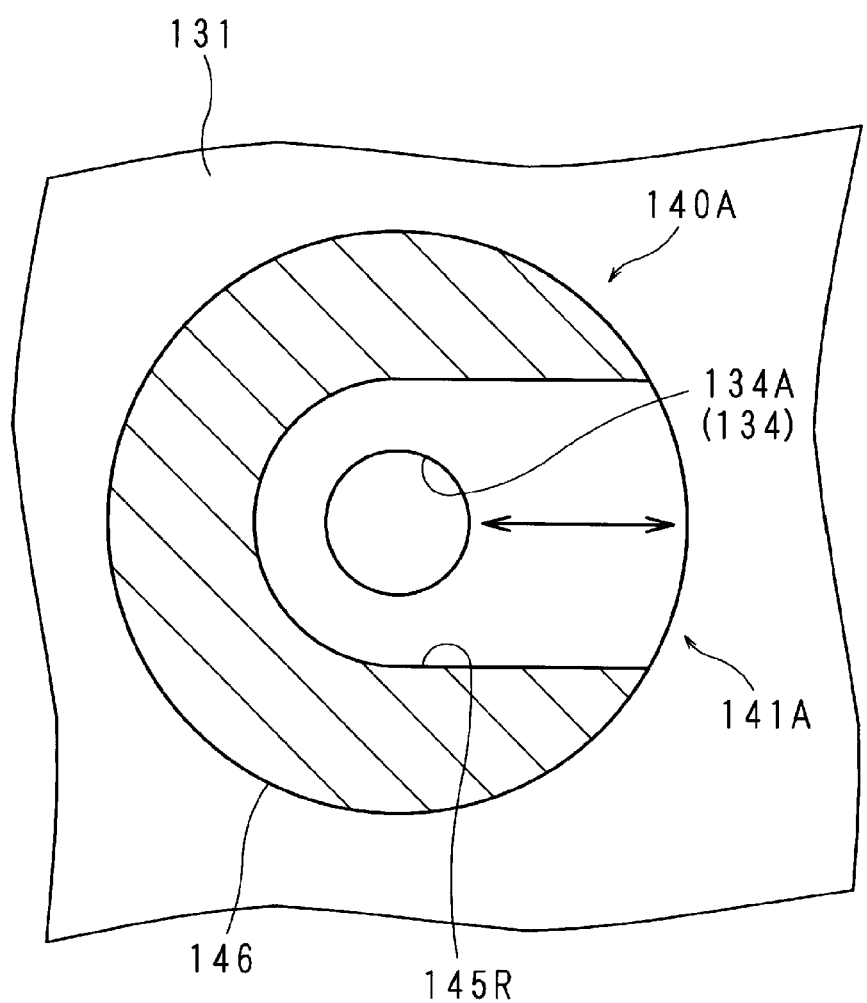
FIG. 13 is a cross-sectional view taken along line XIII-XIII of FIG. 11.

FIG. 11 is a cross-sectional view of the distal end portion 13 taken along line XI-XI of FIG. 10 when the air supply/water supply nozzle 140A is attached to the distal end portion 13, FIG. 12 is a cross-sectional view taken along line XII-XII of FIG. 11, and FIG. 13 is a cross-sectional view taken along line XIII-XIII of FIG. 11.

Unlike the first embodiment, in the second embodiment, the connecting pipe portion, the small diameter portion, and the diameter-reduced portion are provided at the distal end portion 13. The details will be described below.

Inside the distal end portion 13, a connecting pipe portion 136 extending along the longitudinal direction of the insertion portion 14 is provided. Further, the air supply tube and the water supply tube (not illustrated) for sending air or water from the folding portion 16 side to the connecting pipe portion 136 are connected to one end of the connecting pipe portion 136, and communicate with the connecting pipe portion 136. The connecting pipe portion 136 sends the air or water sent through the air supply tube and the water supply tube to an air supply/water supply nozzle 140A side.

That is, the air or water that has flowed into the connecting pipe portion 136 via the air supply tube and the water supply tube is sent to the air supply/water supply nozzle 140A.

A small diameter portion 134 is provided at the other end of the connecting pipe portion 136 on the downstream side via a diameter-reduced portion 135. The small diameter portion 134 has a smaller diameter than the connecting pipe portion 136. The air or water that has flowed into the small diameter portion 134 is emitted through the outlet 141A described later.

As described above, the diameter-reduced portion 135 is formed on the downstream side of the connecting pipe portion 136 and on the upstream side of the small diameter portion 134. The diameter-reduced portion 135 connects the other end of the connecting pipe portion 136 and one end of the small diameter portion 134 (one end opening 134B). The diameter-reduced portion 135 has a tapered shape or a funnel shape. That is, in the diameter-reduced portion 135, the diameter is gradually reduced from the connecting pipe portion 136 toward the small diameter portion 134. Therefore, the pressure of the air or water flowing into the small diameter portion 134 through the diameter-reduced portion 135 is reduced and the flow speed is increased.

Another end opening 134A of the small diameter portion 134 is open to the distal end surface 131, and the lid portion 148A is provided so as to cover the other end opening 134A of the small diameter portion 134.

The semi-cylindrical portion 146 is embedded in the distal end portion 13 except for the end portion on the lid portion 148A side, and the lid portion 148A extends parallel to the distal end surface 131 at the end portion of the semi-cylindrical portion 146. That is, a predetermined range of the distal end surface 131 including the other end opening 134A of the small diameter portion 134 is covered by the lid portion 148A, and a guide path 149A for guiding the air or water flowing out from the other end opening 134A to the outlet 141A is formed. In other words, the small diameter portion 134 is connected to the guide path 149A via the other end opening 134A.

That is, the guide path 149A is a cavity formed by the lid portion 148A, the end portion of the semi-cylindrical portion 146, and the distal end surface 131. The guide path 149A is parallel to the thickness direction of the lid portion 148, and includes a side wall 145R (guide wall) which is the inner surface of the semi-cylindrical portion 146 and the ceiling wall 145C which is orthogonal to the side wall 145R and is the inner surface of the lid portion 148A.

The guide path 149A communicates with the outside through the outlet 141A. The outlet 141A is configured by an edge of the protruding portion of the lid portion 148A, the distal end surface 131, and an edge of the end portion on the lid portion 148A side of the semi-cylindrical portion 146. The outlet 141A has a substantially oval shape.

The air or water that has flowed into one end of the connecting pipe portion 136 is injected through the diameter-reduced portion 135, the small diameter portion 134, the guide path 149A, and an outlet 141A. In FIG. 11, the air or water flow path is indicated by a broken line arrow.

The side wall 145R surrounds the other end opening 134A of the small diameter portion 134 in a U-shape, and guides air or water from the other end opening 134A to the outlet 141A (see FIG. 13). The other end opening 134A of the small diameter portion 134 is, for example, circular, and the side wall 145R is formed at a position separated from the edge of the other end opening 134A in the radial direction of the other end opening 134A.

That is, the inside of the guide path 149A forms a cavity in which the cross-sectional area of the other end opening 134A in the radial direction is larger than the area of the other end opening 134A.

Further, in the endo scope 10 according to the second embodiment of the invention, the portion facing the outlet 141A in the side wall 145R has a bent semicircular shape in the crossing direction (direction of the solid line arrow in FIG. 13) connecting the other end opening 134A and the outlet 141A. That is, in such a portion, since the distance from the edge of the other end opening 134A to the side wall 145R is substantially the same, a cavity having a uniform size is formed. Therefore, the air or water flowing out from the other end opening 134A forms a more uniform vortex flow around the other end opening 134A.

That is, in the diameter-reduced portion 135, the diameter is gradually reduced from the connecting pipe portion 136 toward the small diameter portion 134, so that the flow speed of the air or water flowing into the small diameter portion 134 through the diameter-reduced portion 135 becomes faster. The air or water having a higher flow speed flows out from the other end opening 134A and is guided by the ceiling wall 145C and the side wall 145R to form a vortex flow around the other end opening 134A. Therefore, the air or water diffuses uniformly in the guide path 149A. Therefore, when the air or water is emitted from the outlet 141A, it easily spreads in the width direction, and the injection force at the time of emission can be secured.

The other configurations of the guide path 149A are the same as those of the guide path 149 of the first embodiment, and detailed description thereof will be omitted.

Since it has such a configuration, even in the endoscope 10 according to the second embodiment, the air or water flowing out from the other end opening 134A forms a more uniform vortex flow around the other end opening 134A, and then rectified and emitted from the outlet 141A. After emission, the air or water begins to spread in the width direction, and when it reaches the observation optical system 132, it spreads over a wider area than the area of the observation optical system 132.

Therefore, in the endoscope 10 according to the second embodiment of the invention, the cleaning air or water has a high speed and does not change in speed before and after being emitted from the outlet 141A of the air supply/water supply nozzle 140A, and ejected to the observation optical system 132. Moreover, the air or water ejected from the air supply/water supply nozzle 140 can clean the entire surface of the observation optical system 132 cleanly.

In addition, in the endoscope 10 according to the second embodiment of the invention, the connecting pipe portion 136, the diameter-reduced portion 135, and the small diameter portion 134 are provided inside the distal end portion 13, so that it is possible to provide the air supply/water supply nozzle 140A with a simple configuration.

The same portions as those in the first embodiment are designated by the same reference numerals, and detailed description thereof will be omitted.

The endoscope 10 according to the invention is not limited to the above description.

In the above, the case where one air supply/water supply nozzle 140 is provided has been described, but the air nozzle and the water nozzle may be provided respectively.

In the above description, the case where the air or water is ejected from the outlets 141 and 141A of the air supply/water supply nozzles 140 and 140A has been described as an example, but the endoscope 10 according to the invention is not limited to this. It may be configured such that the air and water are mixed and emitted from the outlets 141 and 141A of the air supply/water supply nozzles 140 and 140A.

REFERENCE SIGNS LIST 10 endoscope
14 insertion portion
132 observation optical system
134, 144 small diameter portion
134B, 144B one end opening
134A, 144A other end opening
135, 143 diameter-reduced portion
136, 142 connecting pipe portion (fluid pipe portion)
140, 140A air supply/water supply nozzle
141, 141A outlet
145, 145R side wall (guide wall)
145A, 145B side wall (facing portion)
148, 148A lid portion

The invention claimed is:

1. An endoscope that is provided with an observation optical system provided at a tip of an insertion portion and a fluid pipe portion for sending a fluid onto the observation optical system, comprising:
   a small diameter portion comprising:
      one end opening to which a fluid from the fluid pipe portion flows and has a diameter smaller than the fluid pipe portion; and
      another end opening having an edge circumferentially surrounding the another end opening, the another end opening being flush with a distal end surface of the insertion portion;
   a lid that covers the another end opening of the small diameter portion; and
   a guide wall provided inside the lid and separated from the edge in a radial direction such that the fluid forms a vortex flow around the another end opening, and guides the fluid from the small diameter portion to an outlet.

2. The endoscope according to claim 1, comprising:
   a diameter-reduced portion that is provided between the fluid pipe portion and the small diameter portion and reduces in diameter from the fluid pipe portion toward the small diameter portion.

3. The endoscope according to claim 1,
   wherein the guide wall surrounds the another end opening in a U-shape.

4. The endoscope according to claim 3, wherein,
   the guide wall includes two facing portions that face each other in a facing direction, and
   a dimension between the two facing portions is equal to or less than a dimension of the outlet.

5. The endoscope according to claim 4,
wherein the another end opening is provided in a middle portion between the two facing portions, and provided at the guide wall in a crossing direction intersecting the facing direction.

* * * * *